(12) United States Patent
Sutton

(10) Patent No.: US 7,024,921 B2
(45) Date of Patent: Apr. 11, 2006

(54) CAPILLARY DEVICES FOR DETERMINATION OF SURFACE CHARACTERISTICS AND CONTACT ANGLES AND METHODS FOR USING SAME

(76) Inventor: Stephen P. Sutton, 155 Avalon Ave., Elkton, MD (US) 21921

( * ) Notice: Subject to any disclaimer, the term of this patent is extended or adjusted under 35 U.S.C. 154(b) by 0 days.

(21) Appl. No.: 10/703,107

(22) Filed: Nov. 6, 2003

(65) Prior Publication Data

US 2004/0187565 A1    Sep. 30, 2004

Related U.S. Application Data

(60) Provisional application No. 60/424,124, filed on Nov. 6, 2002.

(51) Int. Cl.
*G01N 11/04*    (2006.01)
*G01N 13/00*    (2006.01)

(52) U.S. Cl. .................................. 73/54.04; 73/64.48

(58) Field of Classification Search ............. 73/54.04, 73/54.05, 54.06, 54.07, 54.08, 54.09, 64.48, 73/64.52
See application file for complete search history.

(56) References Cited

U.S. PATENT DOCUMENTS

| | | | |
|---|---|---|---|
| 2,363,140 A * | 11/1944 | Persons | 138/40 |
| 4,050,822 A | 9/1977 | Grat | |
| 4,688,938 A | 8/1987 | Demoulin et al. | |
| 4,694,685 A | 9/1987 | Dick | |
| 4,697,451 A | 10/1987 | Matteson | |
| 5,080,484 A | 1/1992 | Schneider et al. | |
| 5,115,677 A | 5/1992 | Martin et al. | |
| 5,121,636 A | 6/1992 | Seiter et al. | |
| 5,137,352 A | 8/1992 | Blitshteyn et al. | |
| 5,143,744 A | 9/1992 | Barth et al. | |
| 5,268,733 A | 12/1993 | Wright et al. | |
| 5,792,941 A | 8/1998 | Rye et al. | |
| 5,838,445 A | 11/1998 | Sandhu et al. | |

(Continued)

OTHER PUBLICATIONS

Product Information Sheet for DuPont Teijin Films™, 3 pages www.dupont.com, Feb. 21, 2002.

(Continued)

*Primary Examiner*—Charles Garber
(74) *Attorney, Agent, or Firm*—Dority & Manning, P.A.

(57) ABSTRACT

Devices are presented which allow determination of unknown surface properties through the creation of a channel capillary, comprised in part of the subject surface or surfaces, and measurement of the capillary pressure created by a test fluid within the resultant channel. In various embodiments of the invention, a channel is created in a reference material which is bonded, through some mechanism, to the test surface in order to create a narrow capillary channel. In other embodiments of the invention, the capillary channel is created with test surfaces on either side of standoff strips which space the surfaces a precise distance from one another. Methods are presented for using these capillaries through immersion, along their length, in a bath of test fluid, such that the resultant fluid level provides a measure of capillary pressure. Being, in part, a consequence of the contact angle between the test fluid and the surface or surfaces under consideration, the capillary pressure is a convenient measure of surface properties inherently related to printability, affinity for adhesives, surface contamination by foreign substances, surface roughness, and the like. Devices are presented which allow measurement of test fluid height within the capillary, both in situations where a static equilibrium is achieved, and in situations where a dynamic contact angle is operative as the fluid rises or falls within the capillary.

29 Claims, 11 Drawing Sheets

U.S. PATENT DOCUMENTS

| | | | |
|---|---|---|---|
| 5,861,946 | A | 1/1999 | Hudson et al. |
| 6,119,511 | A | 9/2000 | Christian et al. |
| 6,230,548 | B1 | 5/2001 | Han et al. |
| 6,270,792 | B1* | 8/2001 | Guillemet et al. .......... 424/443 |
| 6,381,025 | B1* | 4/2002 | Bornhop et al. ............. 356/517 |
| 6,426,392 | B1* | 7/2002 | Chiba et al. ............. 525/326.5 |
| 6,557,427 | B1* | 5/2003 | Weigl et al. ............. 73/863.31 |
| 6,809,828 | B1* | 10/2004 | Bornhop et al. ............. 356/517 |
| 2002/0036140 | A1* | 3/2002 | Manz et al. ................. 204/453 |
| 2002/0068357 | A1* | 6/2002 | Mathies et al. .......... 435/287.2 |
| 2003/0050573 | A1* | 3/2003 | Kuhr et al. ................. 600/567 |
| 2003/0127327 | A1* | 7/2003 | Kurnik ....................... 204/450 |

OTHER PUBLICATIONS

Company Profile on Diversified Enterprises-ADT, 1 page www92.thomasregister.com, Feb. 20, 2002.

UVPS FTP Catalog, 2 pages www.uvprocess.com, Feb. 20, 2002.

Product Information Sheet for Corona-Plus Pro-Dyn Test Ink, 1 page.

Instructions for Using Sherman Test Fluids, 3 pages www.shermantreaters.co.uk, Feb. 20, 2002.

Article—*Corona Treating and the Printing Process*, Thomas J. Gilbertson, GRAVURE, Oct. 2001, 5 pages www.gaa.org, Feb. 20, 2002.

Information Sheet on International Converting Equipment, Inc., 3 pages www.ice-equipment.com, Feb. 20, 2002.

UVPS FTP Catalog—Dyne Pens, 1 page www.uvprocess.com, Feb. 20, 2002.

Miscellaneous Information, Forms, Etc. from Sherman Treaters, 17 pages.

\* cited by examiner

CAPILLARY DEVICES FOR DETERMINATION OF SURFACE CHARACTERISTICS AND CONTACT ANGLES AND METHODS FOR USING SAME

RELATED APPLICATIONS

The present application is based on and claims priority to a provisional application having U.S. Ser. No. 60/424,124 filed on Nov. 6, 2002.

BACKGROUND AND FIELD OF THE INVENTION

In a wide range of scientific, industrial, and medical applications, direct or inferential measurements of the contact angle between a free liquid surface and a solid interface are of great practical importance and value. Given the contact angle at a given liquid-solid interface, it is often possible to utilize known empirical laws to understand and predict a wide range of related physical phenomena. Specifically, the interfacial contact angle, along with fluid properties such as surface tension, viscosity, and density, enable modeling of processes including surface wetting, wicking in pores, and capillary pressure, to name a few. In addition, since the contact angle between a given fluid and surface bears important information regarding affinity for other materials, surface roughness, molecular surface morphology, and the like, any related measurement can prove useful in relative comparisons of surface properties.

Among the many important uses of contact angle data, one particularly common and valuable application involves measurements which provide a relative ranking of how substances will print, bond, or adhere on a given surface. As is well known, surfaces often display varying degrees of affinity for substances which may be fused or bonded to them. Many polymer surfaces, for example, display a general lack of affinity for other materials and are inherently difficult to fuse, bond, adhere, or print with other substances. In such cases, a variety of treatments or coatings are often applied to alter surface compatibility. Measures of surface properties which correlate with the affinity of a given surface to other materials is of value in related enterprises. Contact angle measurements are commonly used for this purpose (to control and gage the effectiveness or surface treatments, for example) since they are known to correlate with surface affinity for other substances and relative compatibility. Various less direct measurements, which correlate to contact angles in some way, find similar use in ranking and comparing the properties of surfaces as they relate to printing, bonding, and adherence with other materials.

Given the vast utility of contact angle measurements, ranging from basic research to practical analysis of printability, the measurement of contact angles has been the subject of extensive investigation, development, and invention. At present, a number of techniques for the measurement of contact angle between a given fluid and surface are well known, and devices are commercially available which utilize these techniques to provide related measurements.

Among the most straightforward of techniques for measurement of contact angles involves the placement of a test droplet on a subject surface and direct observation using optical magnification. The contact angle at the edges of the drop is, thus, directly observed and measured. A wide range of commercial devices currently offer this capability including instruments manufactured by Dataphysics Instruments, GmbH of Filderstadt, Germany, Kernco Instruments co., Inc. of El Paso, Tex., and AST Products, Inc. of Bilerica, Mass.

Another technique involves mounting a subject surface on a fixture which is attached to a microbalance. The surface is then suspended within a test fluid and resulting forces are measured. After properly accounting for buoyant forces, and sample geometries, it is possible to deduce contact angle information from such measurements. In addition, it is possible to measure the angle dynamically, as the fluid surface either advances or recedes over the surface, and utilize this data to compute advancing or receding contact angle. Instruments which perform this type of analysis, thus, provide sophisticated dynamic contact able measurements for innumerable applications ranging from basic research to analysis of bonding and adherence. Any number of analytical instruments of this type are currently available commercially including those manufactured by Kruss, GmbH, Dataphysics Instruments, GmbH of Filderstadt, Germany, and AST Products, Inc. of Bilerica, Mass.

The commercial interest in such instrumentation, and the vast utility of the information they provide, has driven tremendous development in this general area. Examples of developments in the measurement of contact angles and related surface properties are exemplified by U.S. Pat. Nos. 4,050,822, 5080,484, and 5,268,733 which are incorporated herein for reference. U.S. Pat. No. 4,050,822 describes a device which dispenses a droplet of known volume onto a test surface, and allows inference of the fluid contact angle from the measured maximum droplet height above the interface. U.S. Pat. No. 5,080,484 describes a device for measuring the contact angle through the measurement of laser light reflected from the liquid and solid surfaces along a line of contact. U.S. Pat. No. 5,268,733 describes a device which enables determination of contact angle through projection of the image of a droplet onto a screen, and use of a special protractor scale facilitating accurate determination of contact angle.

Although this prior art is sophisticated, and enables accurate determination of contact angles and related information for many applications, associated instrumentation is typically complex and expensive. Although this level of sophistication fills an important need, there is considerable demand for measurement techniques more suited to immediate analysis of surface characteristics in routine analysis. Particularly in manufacturing settings, where quality control metrics are needed for surfaces, but analysis must be carried out quickly and with minimal complexity, there is a need for improved methods. In addition, there is a constant demand for advancement in this general area of surface analysis, and any technique which offers alternatives to current methodology and instrumentation holds the potential to dramatically extend and augment current measurement capabilities.

One alternative which currently exists for immediate gross indications of surface bondability and printability is provided by examination of wetting by a series of different fluids. So-called dyne test fluids are engineered with a range of different surface tensions. These fluids are progressively swabbed or smeared on to a subject surface (sometimes with a specially designed pen), to determine those which bead and those which wet. Although this is not a direct measure of contact angle for any specific fluid on the surface, the surface tension of the fluid which will wet the surface is generally correlated with the contact angle of a given specific fluid. In addition, the result is similarly correlated with affinity for inks and other substances. U.S. Pat. No. 4,694,685, which is incorporated herein for reference, presents a set of water-based fluids with different surface energies but which are nearly identical in other respects (such as viscosity). In addition, Diversified Enterprises-ADT of Claremont, N.H., U.V. Process Supply Inc. of Chicago, Ill., and Vetaphone of Kolding, Denmark, all offer dyne test fluids or dyne test pens for use in the manner described.

Although dyne test fluids are a pragmatic and immediate means for determining surface properties, they provide only a gross and somewhat subjective measurement. In addition, contamination of the fluids, toxicity, and perishability can present a host of issues in practical application.

For all of these reasons, there is a need for methods and devices which augment those currently available for the measurement of contact angles and related information. Where such methods and devices offer extensions of the more sophisticated aspects of current technology, they promise to extend the scope of current measurement capabilities. While, in itself, the value of such extension is clear, there is a further need for any technology which enables simple, cost effective, and accurate measurement of surface properties in routine applications such as quality control.

SUMMARY OF THE INVENTION

It is one feature of the present invention to provide a simple and practical means of measuring surface properties and static contact angles between fluids and a test surface through incorporation within a capillary and measurement of capillary pressure. It is a further feature of the present invention to provide devices and techniques for incorporation of a test surface within a capillary and subsequent measurement of capillary pressure as the fluid advances or recedes to yield a new analytical technique for measurement of dynamic contact angles.

The instant invention, in one embodiment, is generally directed to a device which incorporates the surface or surfaces to be tested within a capillary of known dimensions. The capillary thus created is intended for submersion within a bath of fluid such that the height to which the fluid rises in the capillary, relative to the surface of the fluid within the vessel, may be measured. The fluid height is a measure of capillary pressure and, given the geometry and composition of the capillary, allows calculation of contact angle and inference of related properties.

Versions of this invention may be augmented with an apparatus which enables the surface of the fluid bath to move relative to the capillary, causing the fluid level within the capillary to rise or fall at a given rate. Through measurement of the relative height between the level of fluid in the bath and the height of fluid in the capillary, a dynamic measure of capillary pressure is thus obtained. Just as in the static case, this dynamic pressure may be used to calculate the contact angle with the unknown surface under dynamic conditions, the result being the dynamic contact angle at a given rate of advancement or recession.

DETAILED DESCRIPTION OF THE INVENTION

Figure 1:
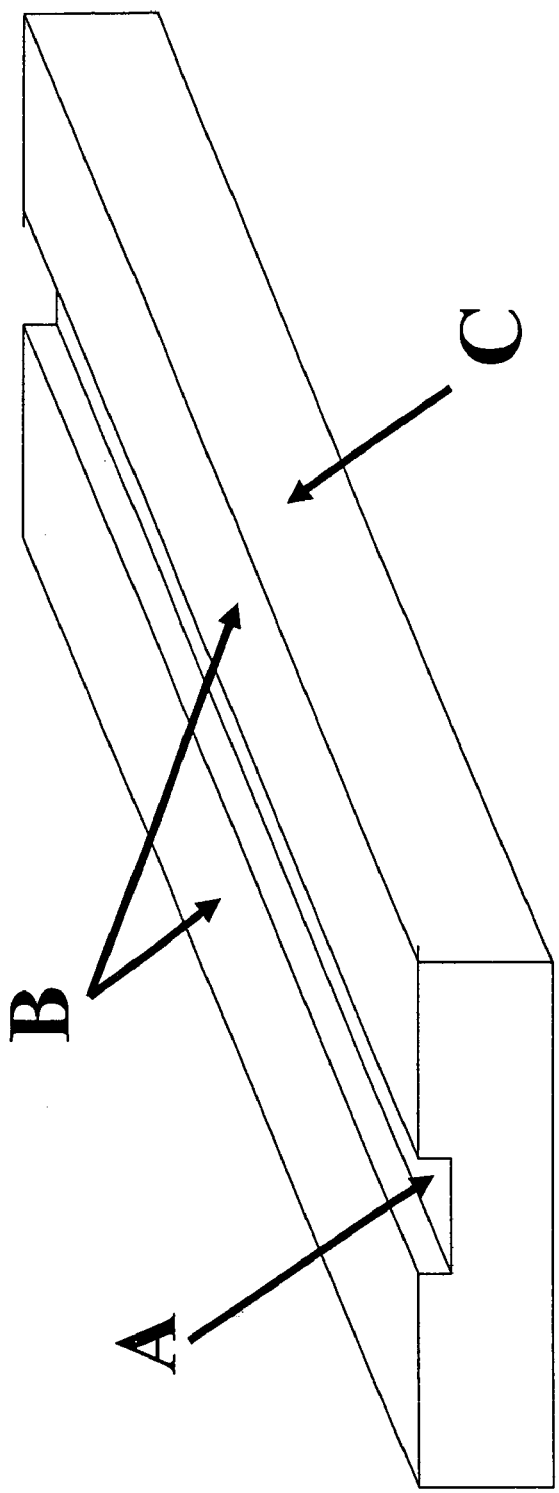
FIG. 1 shows a rectangular reference channel, A, within the surface, B, of a supporting material, C.
Figure 2:
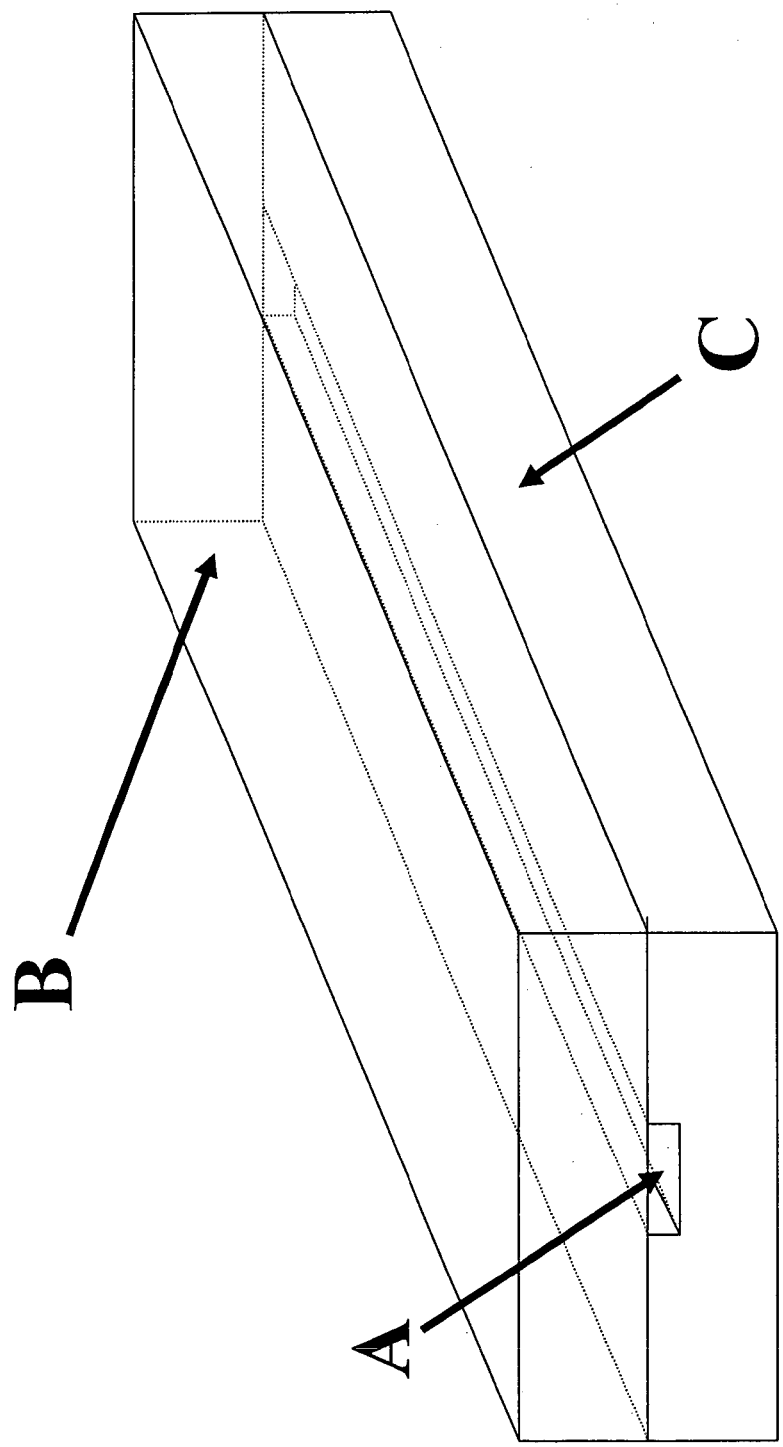
FIG. 2 shows a rectangular reference channel, A, covered by a material for testing, B, to form a channel capillary device, C.
Figure 3:
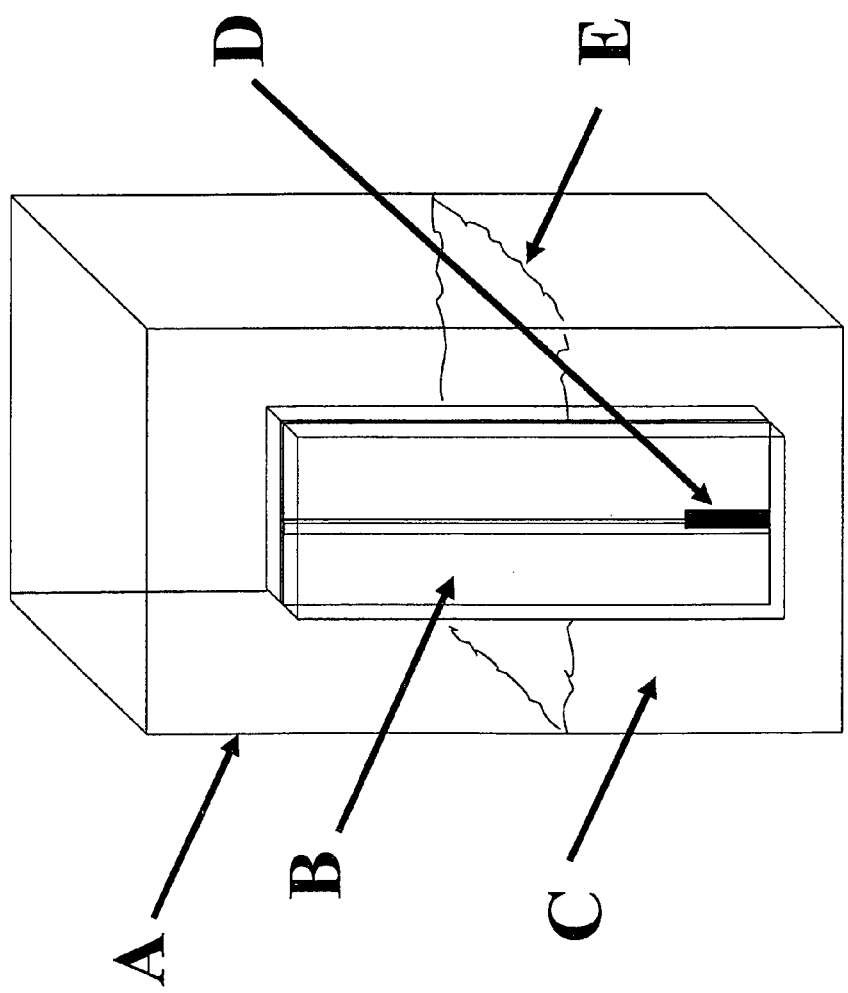
FIG. 3 shows a container, A, in which a channel capillary device, B, is suspended in a bath of reference fluid C. The fluid column within the capillary, D, rises to some height relative to the bath surface, E.

Embodiments of the instant invention serve to create capillaries which enable measurement of the pressure produced by the surface tension of a test fluid and the contact angles it presents at the capillary walls. As one example of this concept, it is illustrative to consider a device including a rectangular reference channel, of known depth and width, within a reference material as shown in FIG. 1. If a surface of unknown characteristics is sealed, through clamping, adhesion, or any other mechanism over this channel, as shown in FIG. 2, the result is a channel capillary, one internal surface of which is the surface to be tested. Upon submersion along its length to some depth within a test fluid, the fluid will rise in the capillary until hydrostatic pressure is balanced by capillary pressure, as shown in FIG. 3. Since the capillary pressure is a consequence of fluid surface tension, and contact angles at the capillary walls, the height of fluid within the capillary is intimately related to these parameters. With proper analysis, fluid height measurements may be used to infer the fluid contact angle with the surface being tested, or simply as a measure of surface properties.

Figure 4:
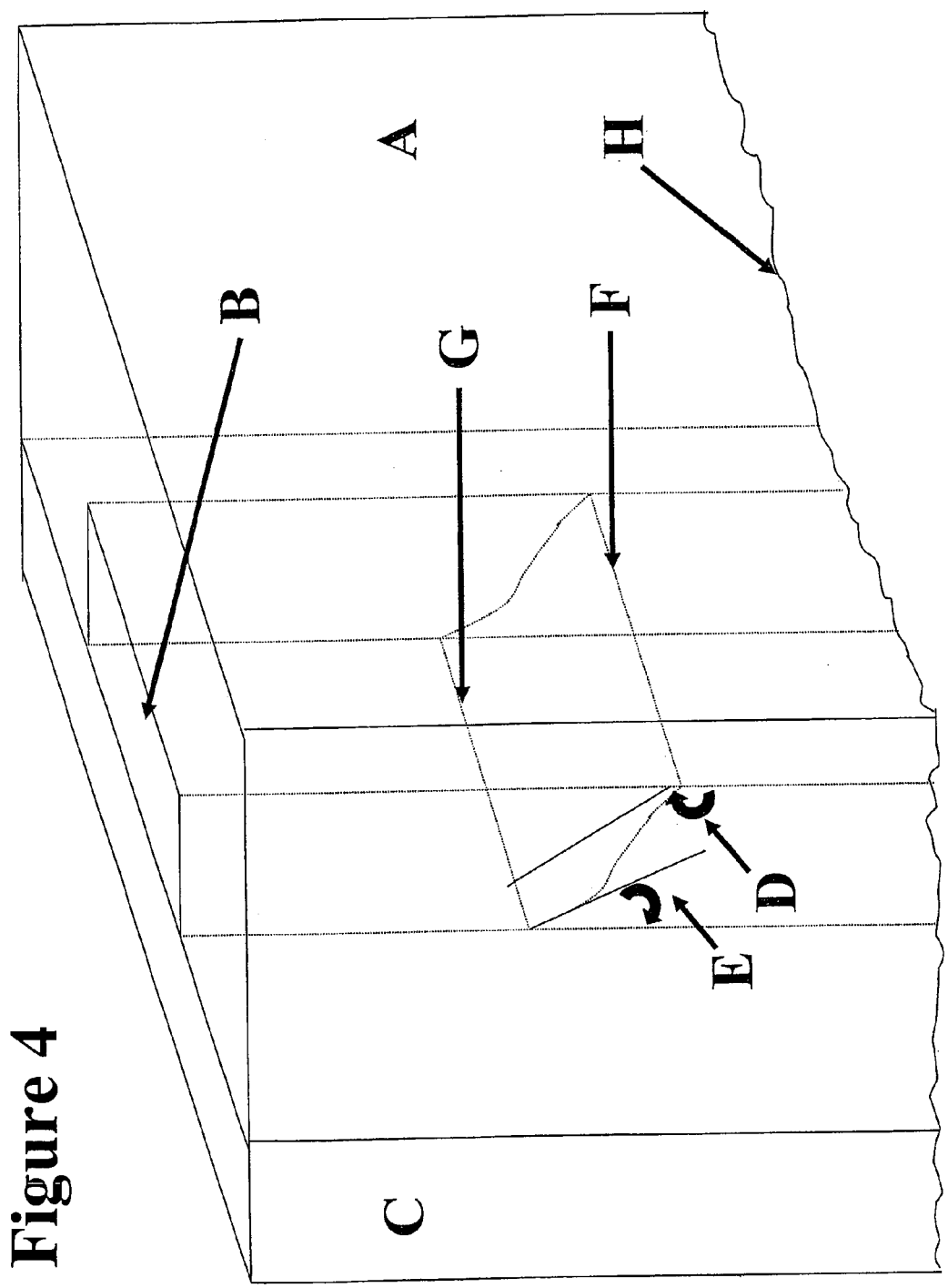
FIG. 4 is a magnified schematic view (not to scale) of the fluid column within a reference channel cavity device. A materials system, A, supports a reference channel, B, which is sealed against a material for testing, C. This forms a closed capillary into which fluid will rise or fall. The fluid contact angle against the reference channel, D, causes the fluid to push downwards (or upwards) along the line of contact, F. The fluid contact angle against the subject surface, E, causes the fluid to pull downwards (or push upwards), along the line of contact between the fluid and that surface, G. These forces cause the fluid to rise (or fall) some level above (or below) the fluid bath surface, H.

Referring to FIG. 4, it is possible to infer the contact angle of the fluid with the test surface through consideration of the exact conditions which exist at the fluid interface in equilibrium. Assuming that the surface tension of the test fluid is given by y, and that the fluid makes a contact angle of $\theta_{known}$ with the surfaces of the reference channel, the surface tension, pulling at the line of contact across the width of the reference channel, exerts a downward force of $$F = yw \cos(\theta_{known}),$$

Where y is the fluid surface tension, w, is the channel width and $\theta_{known}$ is the fluid contact angle with the reference surface.

Similarly, the surface tension of the fluid, pulling at the line of contact across the width of the test surface within the capillary, exerts a downward force of $$F = yw \cos(\theta_{known})$$

on the column of water (where $\theta_{unknown}$ is the fluid contact angle with the subject surface). These forces combine to yield a total resultant force of $$F_{total} = yw(\cos\theta_{known} + \cos\theta_{unknown}).$$

While the two sides of the capillary along its depth also contribute to the total force on the column due to fluid surface tension, these forces may be ignored provided that the depth of the channel is small in comparison to its width. Given this approximation, the capillary pressure may be calculated by considering that the total force acts on a surface with the cross sectional area of the channel, $$A = wd,$$

(where d is the channel depth) to produce an effective capillary pressure of $$P_{capillary} = y/d(\cos\theta_{known} + \cos\theta_{unknown}).$$

In static equilibrium, this pressure must be equal to the hydrostatic pressure within the fluid at the surface of the fluid within the capillary. Hydrostatic pressure, produced by the action of gravity on the fluid, is given by $$P_{hydrostatic} = \rho g h$$

where $\rho$ is the fluid density, g is the acceleration due to gravity, and h is height of the fluid within the capillary above or below the surface of the fluid bath. Equating the hydrostatic and capillary pressures, and solution for the contact angle between the fluid and test surface yields:

$$\theta_{unknown} = \cos^{-1}(\rho g h d/y - \cos\theta_{known}).$$

Given the various fluid properties and $\theta_{known}$, therefore, it is possible to determine the contact angle of the fluid with the test surface.

As one of ordinary skill in the art will recognize, any number of methods may be used to determine $\theta_{known}$. Probably the most straightforward technique involves measurement of the height of fluid within the capillary using a test surface identical to the reference channel. In this case, $\theta_{known}$ is given by $$\theta_{known} = \cos^{-1}(\rho g h d/2y).$$

In addition, two reference channels may be created with different known depths to provide two measurements of fluid height against the same test surface. This gives simultaneous equations in $\theta_{known}$ and $\theta_{unknown}$ which may be solved for each.

Given this analysis, it is clear that the height to which fluid will rise in a capillary device, designed to incorporate a subject surface, is intimately related to the manner in which the fluid interacts with that surface, and the associated contact angle. While such analysis serves to demonstrate important principles, most notably an intimate relationship between measurements enabled by the invention and subject surface properties, the analysis is based purely on a mathematical model with associated approximations and limitations. It is, thus, offered only to facilitate understanding of the linkage between measurements provided by the invention and subject surface properties. While such an analysis, with more or less sophistication, may be utilized to examine physical properties of a surface in connection with measurements provided by the invention, no aspect of such an analysis is essential for many practical applications. Certainly, it is possible to utilize measurements provided by the invention in any number of other more and less sophisticated forms of analysis. In particular, it is possible to simply utilize the devices of the present invention to compare the empirical measurement of fluid heights obtained with different subject surfaces. Further, it is possible in the any manner of more in depth theoretical and or empirical analyses including the verification and study of mathematical models such as the one presented.

Turning to actual embodiments of the invention, there is no constraint that the reference channel possess a rectangular cross section. While a rectangular channel is advantageous for simplicity in contact angle calculations, devices with a wide range of different cross sectional shapes are viable and represent embodiments of the present invention. Specifically, semicircular, semiovular, triangular, and nearly any other form which allows incorporation of the test channel within the capillary, are all viable embodiments. Results obtained using such a system may be used either comparatively (through comparison of results obtained using different surfaces) or quantitatively through appropriate calculation of the contact angle, just as outlined above for a rectangular channel. In some cases, associated calculations may be carried out using computer based numerical methods.

Figure 5:
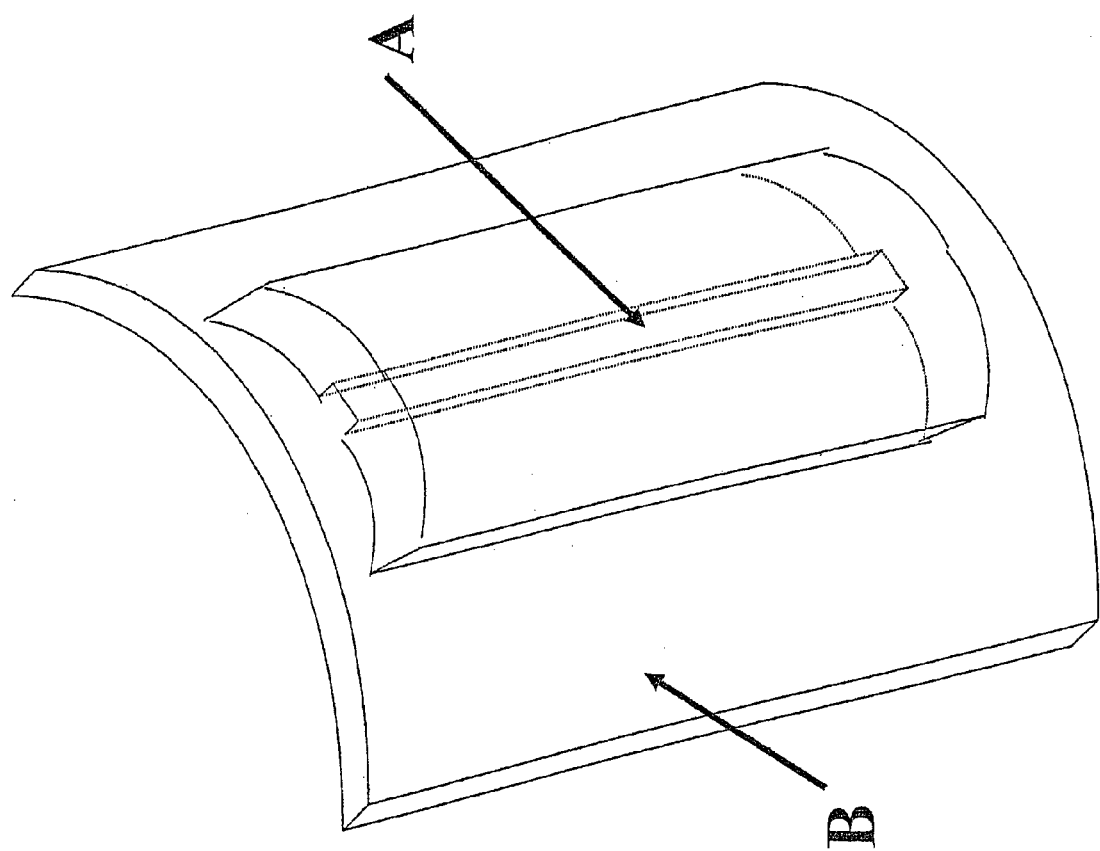
FIG. 5 shows a curved reference capillary device for the testing of curved surfaces. In the figure, a reference channel, A, is embedded within a curved surface in order to allow testing of a curved subject surface, B.

As one of ordinary skill in the art will further recognize, the subject surface may not be planar. In many circumstances, for example, it is desirable to measure the surface properties of plastic bottles, and other articles, which have been molded and surface treated. In such circumstances, the capillary device may be constructed to allow conformation over the contour of the surface. An example of such a device, with a form suitable for testing a surface with cylindrically symmetric geometry, is shown in FIG. 5. Provided the radius of curvature of such a surface is large in comparison to the ultimate capillary depth, capillary pressure is little influenced by associated effects, and the mathematical analysis above may be used for analytical determination of contact angle to within a good approximation. Even in cases where the curvature causes a significant effect, a very similar mathematical analysis may be undertaken and utilized in associated analysis.

Dimensions of useful embodiments of these capillary devices may vary considerably. For most applications, the reference channel should be practical to fabricate with high precision, but also appropriate to produce strong differential fluid height changes in response to differences in test surface characteristics. As one example, ordinary mold machining tolerances, will allow construction of rectangular channels within a tolerance of +−0.0005 inches, while greater accuracy can prove impractical for any number of reasons. In rectangular capillaries, since the height of the fluid within the capillary is roughly inversely proportional to the depth of the cavity, an error in reference channel depth will, approximately, correspond to a proportional error in estimation of the cosine of fluid contact angle with the reference surface. A reference channel 0.005 inches in depth, therefore, could be expected to cause an error in determination of cos ($\theta_{unknown}$) by as much as +−10 percent, given typical fabrication limitations. It is, therefore, typical to arrange the capillary depth such that fabrication tolerances yield acceptable results. In general, channels having a depth around 0.015 inches are optimal for many practical applications since this depth yields a strong fluid height change across the range of test surfaces typically encountered (on the order of greater than 1 inch of possible range).

The width of a reference channel may also vary over a wide range. It is important to recognize, however, that analysis may be simplified, and sensitivity improved, if the width of the channel is large in comparison to its maximum depth. In channels of rectangular cross section, for example, the fluid in contact with the side walls of the channel will contribute to the forces acting on the fluid column (which are not a consequence of interaction with the test surface under consideration). In theoretical analysis of capillary pressure, computations are simplified if these side wall forces, and the effects at the wall corners, can be ignored to within a reasonable approximation. Such an approximation, as incorporated into the theoretical analysis presented above, is appropriate if the capillary width is large in comparison to its depth. Provided the ratio of the capillary width to its depth is approximately 10 or greater, the resultant error in calculation of forces is on the order of 10 percent or less, leading to generally acceptable results.

Although channels of great width are desirable, given the considerations above, other factors can limit the utility of channels of very great width. Most importantly, as the channel width becomes very large, relative to the channel depth, mechanical rigidity of the device can become a serious concern. Since even a slight deformation of a few thousandths of an inch can lead to results biased by a substantial error, it is typically desirable for the channel to be self supportive during use, and that undo variations in capillary depth not result from mechanical deformation under the action of stresses created by the fluid, and support of the device during use. While some materials of construction are sufficiently rigid to prevent such deformation, and the reference channel may be fabricated within a thickness of material sufficient to minimize deformation effects, it is typically desirable to limit the width of the channel for the sake of rigidity and mechanical stability. Preferably, it is desirable for the channel width to be less than 1000 times the maximum channel depth. More preferably, the channel width is less than 100 times the channel width and, most preferably, the channel width is less than 20 times the channel width.

While these general geometrical guidelines are provided for the sake of understanding and illustration, they are in no way intended to limit the scope of the present invention. In any number of special circumstances, the height of a reference channel may be arranged to provide a large signal and be extremely small (perhaps under 0.001 inch). In addition, there are circumstances where the channel depth could be quite large to facilitate great relative accuracy in channel dimensions while producing a small, but measurable, height difference for different surfaces.

Given these fundamental concepts and geometrical considerations, embodiments of the capillary devices associated with the invention must also facilitate the incorporation of a subject surface into one or more walls of a capillary with known geometry. For instance, two distinct practical embodiments of such a device are as follows. In the first, an open reference channel, having a cross-sectional profile of arbitrary, but known, form, may be embedded within the surface of a material such that the subject surface may be sealed on top to create an appropriate capillary. Herein, such a device will be referred to as an open channel device. Secondly, the device may include two spacers, of a given thickness, which may be sealed between two surfaces (at least one of which is the subject surface), to create a channel capillary of known thickness. Herein, such a device will be henceforth referred to as a spacer wall capillary device.

Figure 6:
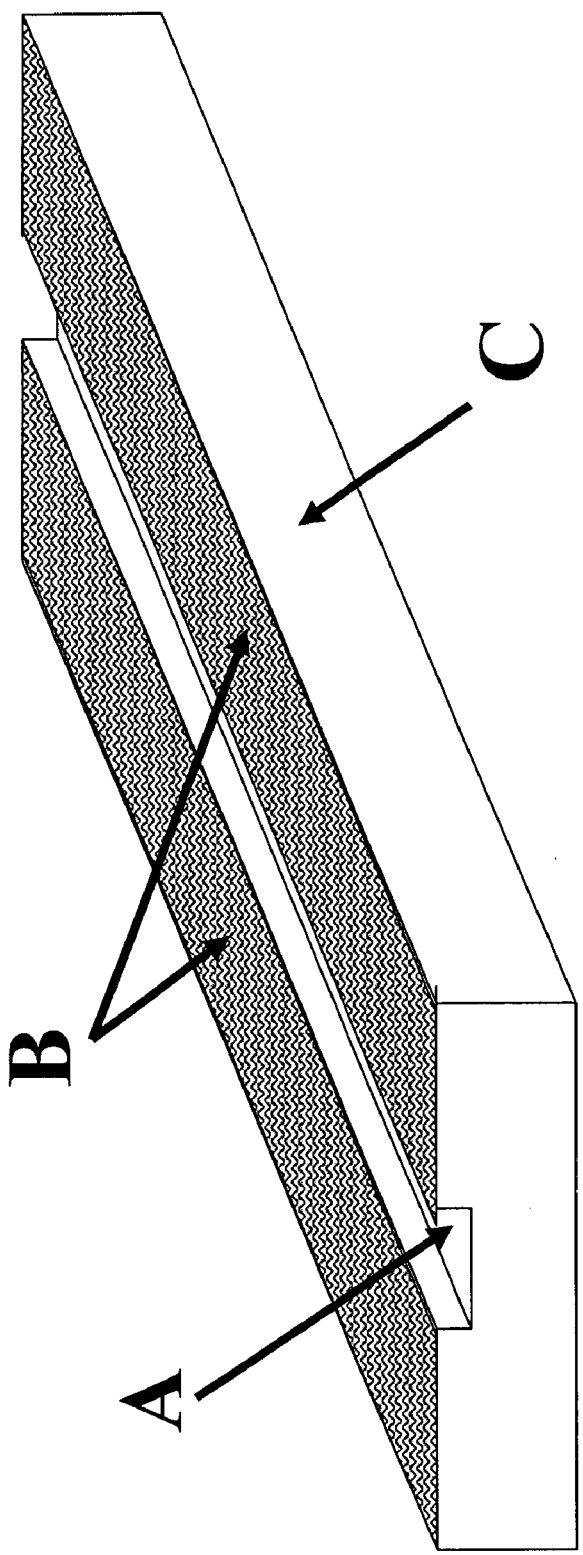
FIG. 6 shows a reference channel capillary device wherein a reference channel, A, embedded within the flat surface of a material, C, is covered on its upper surfaces, excluding the reference channel, with a pressure sensitive adhesive, B.
Figure 7:
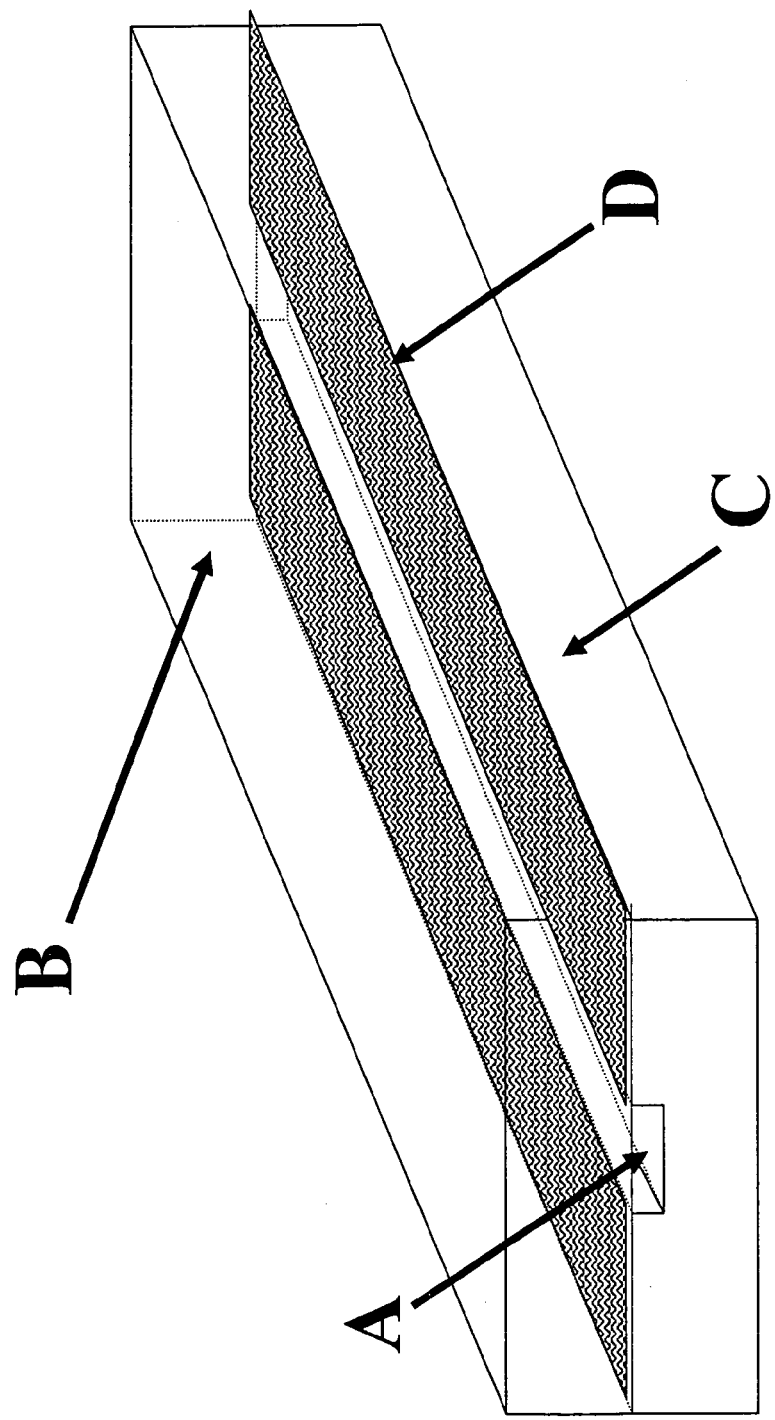
FIG. 7 shows a reference channel capillary device wherein a reference channel, A, embedded within the flat surface of a material, C, is covered on its upper surfaces, excluding the reference channel, with a pressure sensitive adhesive, D. The subject surface of a plate, B, is bonded to the pressure sensitive adhesive to form a closed capillary which is ready for submersion and testing.

The materials of construction for practical embodiments of open channel devices can vary according to the exact needs of a specific application and may include a variety of composite or laminate structures. It is possible, for example, to fabricate a reference channel device into the surface of a plate of glass. Coating of the glass surface (exclusive of the reference channel) with a pressure sensitive adhesive, as shown in FIG. 6, allows convenient attachment of a subject surface as shown in FIG. 7. It is also possible to construct reference channel devices into the surface of various polymer plates, tapes, etc. and to attach the subject surface using pressure sensitive adhesives or the intrinsic adherent properties of a given base material. Nearly any base material is suitable, provided it offers sufficient mechanical stability, does not dissolve, react, or otherwise interact in some undesired fashion with the test fluid, and may be bonded, through some mechanism, to subject surfaces.

Specific materials of construction for reference channel devices can be selected from many different substances, depending on the desired mechanism for attachment of the subject surface, test fluid properties, etc. Provided a means of attachment (which may include adhesives, mechanical attachment, or any form of bonding appropriate to seal the subject surface over the reference channel) reference channel devices may be constructed of metal, glass, ceramic, semiconducting, or polymer base materials. Metals may include, but are not limited to, stainless steels, carbon steels, aluminum, brass, titanium, platinum, gold, copper, lead, graphite or other carbon morphologies, silver, bronze, and low melting alloys such as various grades of solder.

Various grades of glass may be employed including, but not limited to, borosilicate formulations, fused silica, and the like. Ceramics and related composites base materials may include, but are not limited to, silicon carbide based composites, silica-alumina composites, zeolites, clays, and the like. Semiconducting materials such as silicon in particular, and doped or coated similar semiconductors, may further be employed as a material base. Finally, polymers suitable for use as base materials may include, but are in no way limited to, PTFE, co-polymers with TFE, fluopolymers and rubbers, LDPE, HDPE, PET, PPE, PS, PC, Polyamides, Polimides, Thermoplastic Elastomers (including SIS, SEBS, Polyetheresters, or any other block copolymer TPE formulation), Thermoplastic Polyurethanes, Vulcanized rubbers (including polyisoprene rubber, latex rubber, silicone rubber, and polyurethane), and the like.

The surface of the reference channel in such devices, which makes contact with the test fluid, may simply be the exposed surface of the supporting material. Many other constructs are also useful, however, including a reference channel formed within a suitable supporting material such as glass, but which is coated with a second material. Using this technique, a wide range of coatings are possible which may offer different contact angles with water, different chemical properties (for exposure to different fluids), etc. Coatings may comprise, but are in no way limited to, polymers applied through solvent, aqueous, or dispersion methods, silanes, thermoplastic and thermosetting materials, etc. Where polymer substrates are used, surface treatments such as flame treatment, corona treatment, plasma treatment, or chemical deposition of a thin layer of metal, or other material, may be utilized to create a desired surface. Finally, particularly where glass, ceramic, metal, or semiconductor surfaces are employed, all manner of coatings, applied through chemical vapor deposition, vacuum evaporation, sputtering, etc. may be utilized.

In the design of a specific reference channel device, the optical clarity of base materials and coatings can be an important consideration, depending on the optical properties of the subject surface/material and the desired method for measuring the fluid column height during use. Where the fluid height must be measured through direct optical observation of fluid height, it is necessary for either the subject interface, or the reference channel device itself, to be sufficiently clear to allow such observation. In cases where the subject surface/material does not facilitate visual or optical observation of fluid within the capillary, it is necessary to construct the reference channel device of materials which are sufficiently transparent, and using techniques which produce surfaces sufficiently smooth to allow through observation. Certainly, constraints on optical clarity can be alleviated through incorporation into the capillary device some means for measuring fluid height within without the requirement for direct observation. Such means can include, but are not limited to, sensing of electrical resistance or impedance of the fluid column, sensing of electrical resistance or impedance of a film coated within the reference channel, acoustic sensing of the fluid height, etc.

For general application in many practical scenarios, such as testing of polymer films to determine printability and the like, it is desirable for reference channel devices to be fabricated in the surface of a flexible, clear, strip of material which will adhere to smooth surfaces. In one embodiment, we have found that highly plasticized thermoplastic elastomers, including styrene ethylene-butylene styrene (SEBS) rubbers plasticized with mineral oil, are particularly well suited to this purpose. Specifically, mineral oil plasticized SEBS rubbers may be molded, through various techniques, to produce a test strip, containing a reference channel, which will lightly adhere to a subject surface owing to the natural adherent character of such rubbers. Being translucent to extremely clear, test strips comprised of such materials are easily attached to a subject surface and submersed in water to obtain quick results.

Oil plasticized SEBS rubbers suitable for use in the fabrication of such test strips range in hardness from a Shore A of greater than 30 to those with extreme plasticazation producing hardness values immeasurable on the Shore A scale. Polymers suitable for use in such formulations include, but are not limited to, the Kraton G series of thermoplastic elastomers. These polymers may be plasticized in the range from about 50 percent by weight oil to in excess of 90 percent by weight oil. As is common practice with block co-polymer thermoplastic elastomers which physically crosslink due to stryrenic end blocks, a wide range of oils with low aromatic content are appropriate for use in these formulations. The entire DP series of oils, manufactured by Lyondell lubricants, Inc., for example, are well suited for formulation of specific embodiments.

Specific formulations of thermoplastic elastomers, useful in reference channel devices, may incorporate, beyond the base polymer and plasticizer, minor components which modify mechanical and surface properties as desired. The incorporation of parafin wax, for example, is useful in modifying the surface properties of a test strip to render it more hydrophobic and, in some cases, improve other attributes which influence the utility of resulting capillary measurements.

As is commonly recognized, the contact angle between a specific fluid and a solid surface is often dependent upon the rate at which the fluid front advances or recedes over that surface. In addition, a wide range of related phenomena are possible and, in some cases, result in apparent changes in contact angle over time in given system. The contact angle at the edges of a sesile drop of fluid placed on a solid surface can, for example, drift dramatically over time due to a variety of dynamic effects. If such effects occur at the surfaces of a reference channel device, or at the surface of the material being tested, the height of fluid within the capillary will be observed to be dynamic. In fact, such effects are almost always present to some degree. If purely a consequence of the reference channel surfaces, however, and of significant magnitude and duration, these effects can limit the utility of the device or dictate analysis of the dynamics in order to determine contact angle as a function of time, or some related normalization.

For this practical reason, it is often desirable for reference channel surfaces to display minimal contact angle dynamics, or dynamics which die away quickly, allowing immediate achievement of a static condition. When employing SEBS rubbers to construct the reference channel, a wide range of additives may influence the dynamics of contact angle at their surface, making optimization of formulation desirable. While the range of possible additives is extremely large, and any number of related optimizations are feasible, we have found that the addition of parafin wax tends to minimize contact angle dynamics within a given oil plasticized SEBS formulation. In concentrations ranging from about 1 percent by weight to about 10 percent by weight (as a percentage of overall formulation weight), the addition of wax tends to minimize the effect of contact angle dynamics, improving characteristics of resulting capillary devices.

A wide range of manufacturing techniques may be used to produce reference channel devices. In general such methods are dictated by the materials of construction and simply must be appropriate to produce the desired capillary structure within the base substance. In the case of many metals, plastics, some ceramics, and even glass (with diamond tooling), general machining techniques may be employed including CNC based methods. For metals, electrical discharge machining may be utilized. Etching and related chemical processes may be similarly employed, given a base material which may be removed through some chemical or electrochemical process. In the case of materials which may be processed in molten or liquid form, such as plastics, a very wide range of molding methods may be used including, but not limited to, injection molding, centrifugal molding, blow molding, and molten or solvent casting. Finally, continuous processes may be employed to produce embodiments of the invention such as extrusion casting onto a roll with the reverse image of the desired capillary therein, or calendering or calendering to continuously impress a reference channel within sheet, film, or tape stock of metal or polymer which may be subsequently cut into individual strips of a given length.

In spacer wall embodiments of the present invention, somewhat greater flexibility in the materials of construction may be possible. In general, this specific embodiment only requires that materials of construction space the working surfaces within the capillary an appropriate distance apart, seal against the face of these surfaces, and not solvate in or contaminate the test fluid in any manner. For this reason, it is generally possible to construct such a device from nearly any material which may be fashioned to precisely produce an appropriate spacer wall and, through some mechanism, may be bonded to the working surfaces in order to form a capillary. Preferably, such devices are constructed of metal, glass, or polymer strips which are coated with some type of adhesive (typically a pressure sensitive adhesive). Some embodiments of this type provide self-adherence, and are comprised of an SEBS formulation as described above for use in the fabrication of reference channel devices.

Figure 8:
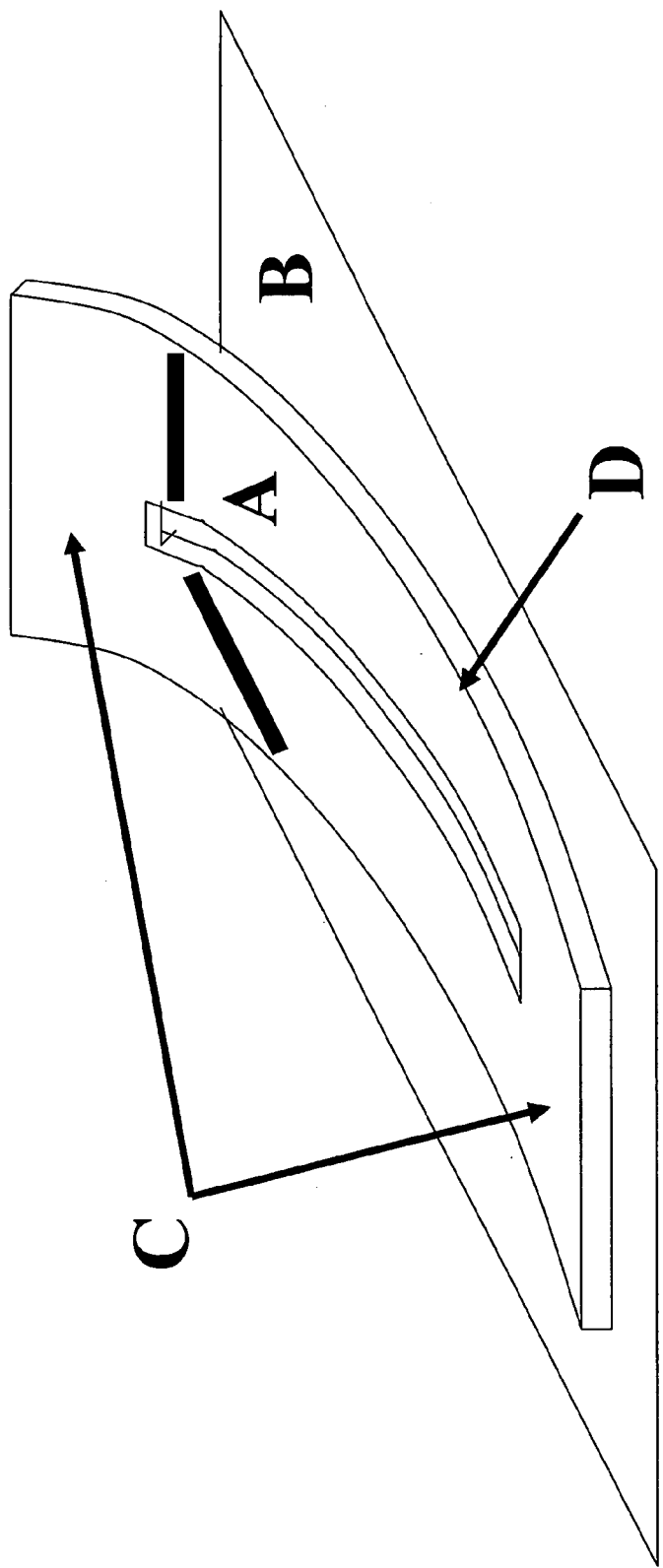
FIG. 8 shows a spacer wall capillary device wherein the flexible spacer walls, A, are applied to a subject surface, B, while held at their ends by tabs, C. This spacer system is easily created by cutting a rectangular section from a strip, D.

Spacer wall devices are most preferably constructed to facilitate ease of application to the working surfaces of the capillary. As shown in FIG. 8, for example, one specific embodiment is comprised of a rectangular sheet, wherein a strip of material has been removed to create a rectangular void.

Such a construct allows the user to apply the device to the working surfaces while the ends provide tabs which conveniently maintain spacing of the sidewalls during application and tabs for manual gripping. Following application, the closed ends of the resultant capillary may be cut away to create a capillary appropriate for submersion in the test fluid.

Extensive investigation has shown that both reference channel and spacer wall embodiments are useful for a broad range of specific measurements and methods of analysis. Specifically, once a subject surface is incorporated within a capillary device, submersion of the resultant capillary, along its length, in an appropriate vessel, causes fluid to rise within the channel. The height of fluid within the capillary following submersion (at a given time) may be utilized, through a variety of techniques, to deduce various subject surface characteristics and parameters relating to the affinity of the test fluid for the surface (such as contact angle).

Given the illustrative theoretical analysis presented above, one obvious method for analyzing surface characteristics from fluid height measurements involves calculation of contact angle using theoretical principles. As outlined above, the contact angle may be directly deduced from consideration of forces acting on the fluid column within the capillary. In devices wherein one working surface of the capillary channel is not the subject surface (as in a reference channel device), deduction of contact angle at the subject surface begins with a determination of contact angle made between the test fluid and the working surface of the channel. This may be accomplished through height measurement in a capillary comprised of the reference channel in contact with an identical test surface. The reference surface contact angle may also be deduced through analysis of results obtained from at least two measurements of fluid height using reference channels with different dimensions or geometries. Once this contact angle has been determined, theoretical analysis allows determination of the contact angle between the fluid and a given subject surface.

This method has been shown to allow deduction of the contact angle between a test fluid and a given surface, and thus, to allow characterization of various surface properties which are a function of this parameter. It is possible, for example, to rank the relative bondability, printability, and general affinity of a subject surface for other materials using contact angles, deduced through the methods described, against a given test fluid. In addition, it is found that contact angles thus calculated may be utilized to determine whether contaminates are present on a given surface (the presence of oil or other organic contaminates on glass surfaces, for example, is easily deduced from the contact angle thus obtained). Finally contact angle measurements, obtained through this method, are useful in determination and characterization of surface roughness, through comparison of contact angles obtained for a given subject surface against that obtained against a reference surface of known roughness or surface morphology.

Beyond direct computation of contact angles, another method for utilizing embodiments of the present invention involves comparative analysis of fluid height measurements as a means for characterization of surfaces. In this method, the height obtained using a given channel device is determined using a series of reference surfaces of known characteristics. Comparison of the height obtained using a given subject surface is then compared to the reference values. In this manner, relative determination of printability, bondability, surface roughness, surface contamination, or any other aspect of surface physics related to contact angle can be accomplished.

Finally, it is important to recognize that the above methods are not only applicable in situations where static equilibrium has been achieved, but also extend to situations involving dynamic contact angles. Of particular importance, it is possible to compute, or make relative comparisons of, dynamic contact angles using the embodiments of the invention.

Figure 9:
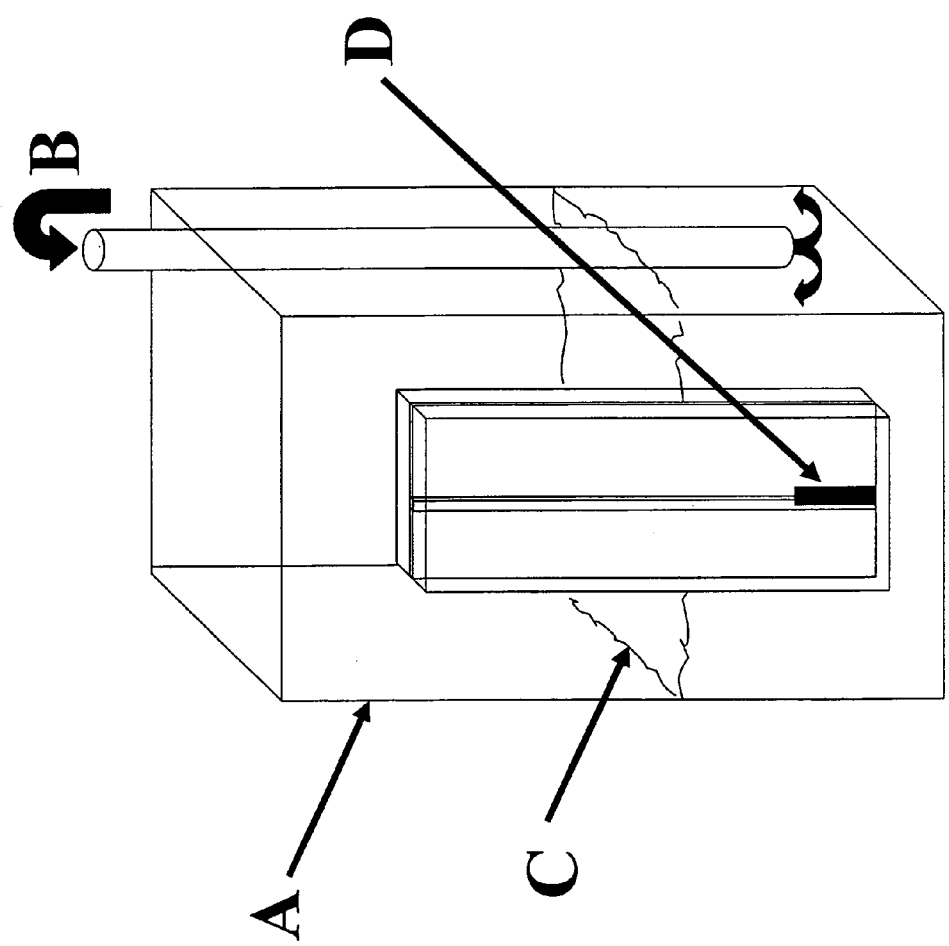
FIG. 9 shows a system for causing fluid to advance within a capillary device. Fluid is pumped, at a given rate, into a vessel, A, through the tube B. This causes the surface of the fluid, C, to rise. The resultant column of fluid within the capillary, D, will, thus, rise to create dynamic advancement of the fluid interface at the capillary walls.

One particularly powerful method for analyzing dynamic contact angles using embodiments of the present invention involves the creation of an advancing or receding fluid height within the capillary. As shown in FIG. 9, this may be accomplished by submersion of the fluid in bath of fluid which, through pumping to add or remove fluid, is induced to change level at a given rate. As a result, the fluid height within the capillary will be induced to change at a specific rate. The height of the fluid within the capillary at a given instant, relative to the moving level of fluid in the bath, provides a measure of capillary pressure created by the dynamic contact angle in a manner exactly analogous to that presented above for the static situation. In some cases, a correction is needed for the pressure required to cause the fluid to flow into, or out of, the capillary as a result of viscous drag. In any case, it will be obvious to one of ordinary skill in the art that such a method enables measurement of dynamic contact angles and related phenomena. Just as in the static case, either direct theoretical analysis, or relative comparisons can be undertaken.

Figure 10:
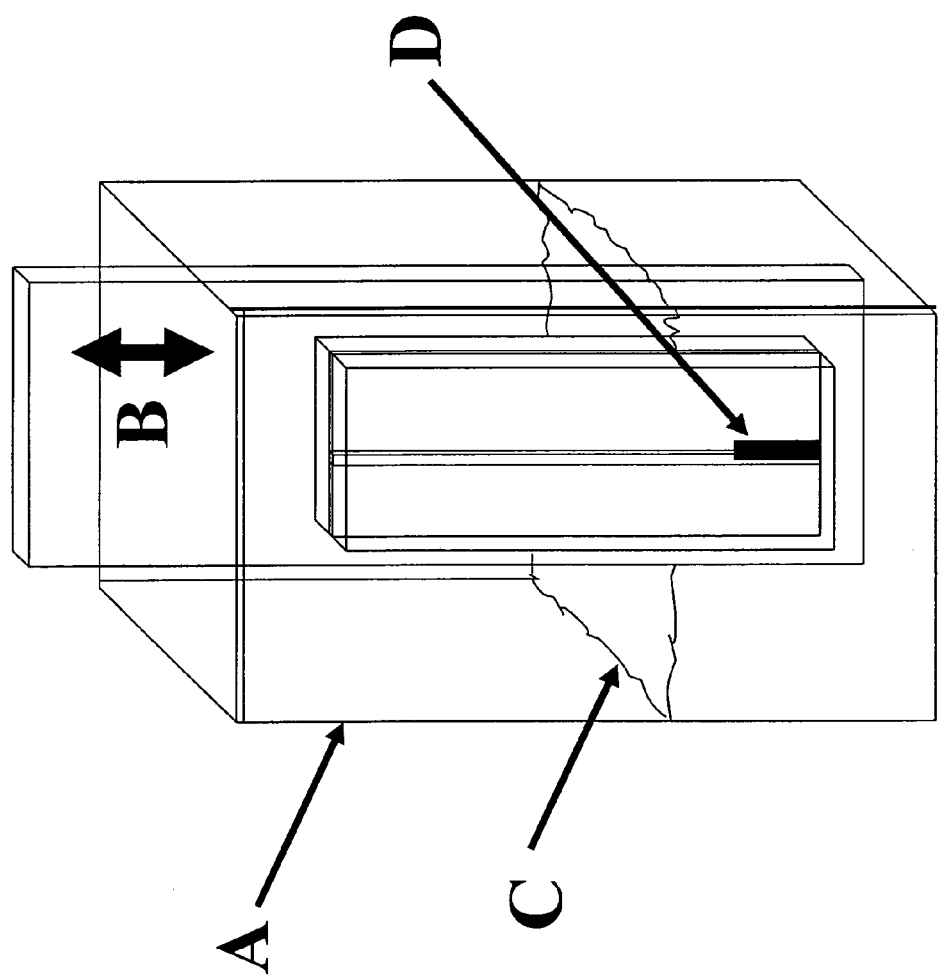
FIG. 10 shows a system for causing fluid to advance or recede within a capillary device. Within a vessel, A, a mechanical stage, B, is caused to move up, or down, relative to the surface of the test bath, C. The column of fluid within the capillary will, thus, advance or recede over the capillary walls to enable dynamic measurements.

It will further be obvious to one of ordinary skill in the art that the creation of a dynamic fluid height within the capillary device can be accomplished though a variety of techniques. Specifically, the capillary can be affixed to a stage which moves, along the capillary length, into, or out of, a test fluid bath as shown in FIG. 10. Any manner of similar techniques involving tipping or rotation of the bath, etc. may also be employed.

In order to measure the relative height of the fluid within the capillary in such dynamic circumstances, it is possible to use any manner of appropriate instrumentation and methodology. One of the most practical techniques involves time lapse video imaging of the capillary during a dynamic experiment coupled with either real time, or subsequent, analysis to determine the relative height. In addition, more advanced methods for measurement and inference of the dynamic height, including but not limited to, resistance or impedance measurements of fluid within the capillary and bath, acoustic measurements of height, and the like, may all be employed in this regard.

EXAMPLE 1

A reference channel device, with a rectangular channel cross section, was fabricated using oil plasticized Kraton G 1650 SEBS rubber.

Figure 11:
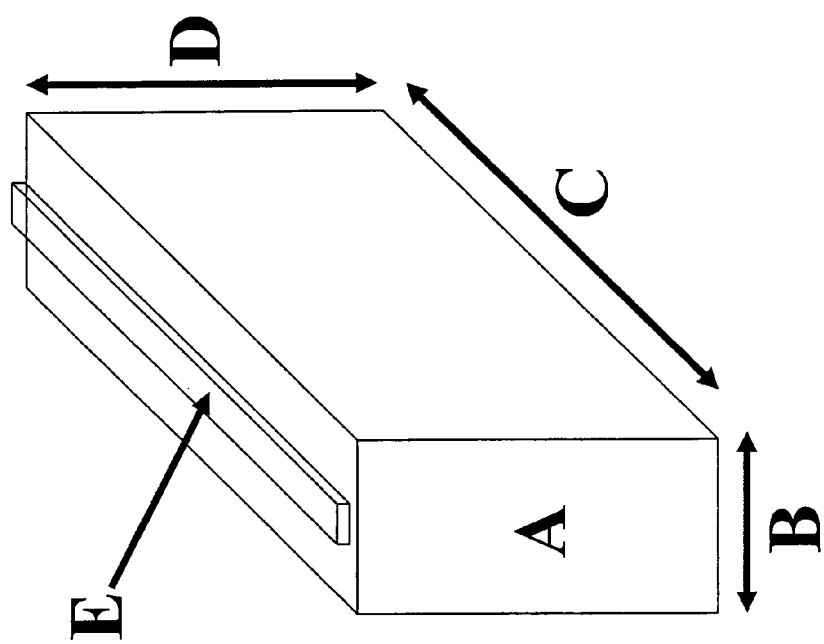
FIG. 11 shows a schematic of a mold used to cast a reference channel device. The mold may be constructed from a block of 17-4 stainless steel, A. The width of the mold, B, may be 0.8 inches, the length, C, may be 8.0 inches, and the height, D, may be 2.0 inches in one embodiment. A step on one of the long sides of this block, E, may be machined to a height of 0.015 inches and a width of 0.150 inches.

To enable the fabrication, a mold was machined out of a block of 17-4 stainless steel alloy. This mold was rectangular, having a length of 8.000", a width of 0.850", and a depth of 2.000". Along one of the 8.000"×0.850" faces of this mold, a raised step was created measuring 0.015" in height and 0.150" in width. FIG. 11 shows a schematic drawing of the finished mold. This mold was highly polished, using fine diamond compound, to achieve a mirror polish on the face with the raised step.

10 grams of Kraton G 1650 polymer was measured into a sample cup along with 1) 5 grams of Walnut Hill, Inc. general purpose and industrial paraffin wax and 2) 85 grams of Lyondel Lubricants inc. DP500 mineral oil. The resultant compound was thoroughly mixed and placed in a glass dish. This dish was then placed in a laboratory oven at a temperature of 175 degrees Celsius for 30 minutes. The material was thoroughly stirred every 10 minutes during heating. This resulted in a molten liquor of sufficiently low viscosity to allow liquid casting of a reference channel device.

The top of the mold was wrapped with PTFE pipe thread tape to create a dam approximately 0.1 inch high around the edge. The molten compound was removed from the oven and immediately poured onto the mold (which was at ambient temperature). The thermoplastic elastomer casting was allowed to cool for approximately 4 hours. The PTFE tape was peeled from the edge of the casting and the resultant rubber article was removed from the mold surface. This procedure produced a very soft, translucent rubber strip, approximately 8 inches in length, and 0.1 inches in thickness, having a rectangular reference channel down the length of one surface approximately 0.015 inches in depth by 0.150 inches in width.

In order to verify the depth of this channel, and examine any deformation which might occur when attached to a surface, a 2 inch strip of this material was cut from the casting and attached to the side of a flat-machined stainless steel surface. Using a Unitron toolmakers microscope, the opening of the capillary channel created against the steel surface was observed from one end. Using the translation micrometer to move the stage and measure the depth of the channel, the channel depth was measured to be within 0.0002 inches of 0.015 inches. The channel depth, therefore, in all subsequent calculations, was taken to be 0.015 inches.

In order to test this article, and compare differences in test fluid height within capillaries created against surfaces with different properties, various standard polymer films with different characteristics were tested. A rectangular acrylic vessel, 4.00 inches in height by 2.00 inches square, was thoroughly cleaned with HPLC grade deionized water (GFS Chemicals, Inc. cat. # 1963 Stock # 76702). A swatch was cut from the surface to be tested, and the surface was adhered over the thermoplastic elastomer reference channel. In all cases, the natural tendency of the thermoplastic elastomer to form a light bond with the surface was used for adherence. A scale, marked in millimeters, was affixed to the outside of the acrylic vessel and the assembled capillary was affixed to the inside the vessel, behind the scale, using the natural adherence of the unused side of the thermoplastic elastomer strip. A CCD camera was focused on the system and the camera signal was input into a computer system allowing time lapse photography of the subsequent experiment. HPLC grade water at a temperature of 22 degrees Celsius was then poured quickly into the vessel to a predetermined height, bringing the water test fluid bath approximately 1.5 inches above the bottom of the capillary channel. Using the computer, images of the system were digitally acquired at a rate of 6 per minute.

Using this method, a series of different surfaces, having varying affinity for water, and general bondability/printability, were tested. The surfaces chosen were intended to cross a broad range of related effects, and to encompass materials commonly tested and surface treated to enhance bondability. In some cases, polymer surfaces were tested in both a virgin non-treated state and following corona treatment providing a one to one demonstration of associated effects.

The specific surfaces tested were as follows:

1) PTFE pipe thread tape (Webstone Inc., Worcester, Mass. # 05262)
2) Untreated High Density Polyethylene Film (Untreated side of Film Supplied by Griff Inc., Bristol, Pa. # 2147-03)
3) Backside of a strip cut from the thermoplastic elastomer casting from which the reference channel device was cut
4) Untreated Low Density Polyethylene Film (Untreated film supplied by Griff Incorporated # 1217-03.06)
5) Corona Treated High Density Polyethylene Film (Treated side of 15 mil film supplied by Griff Incorporated # 2147-03)
6) Polyester Film (Untreated film supplied by Griff Incorporated # 1713-17*R)
7) Flame treated glass microscope slide (free of organic contaminates)

A sample of each of these surfaces was tested using the methods outlined above. Subsequently, the resulting digital time lapse video was examined in detail to determine the water height, relative to the bath level in the acrylic vessel, as a function of time.

In all cases, dynamics was observed over a period of approximately 120 seconds following submersion of the capillary opening by the water surface. Largely, a static equilibrium was observed beyond this period extended up to observational limits of 1 hour.

The static fluid height, 120 seconds following submersion, measured relative to the water level in the bath, is listed for each surface tested in the table below (positive values are above the level of the bath and negative values represent depression of the level within the capillary below the bath level).

| Material | Height |
|---|---|
| (1) | −29.0 mm |
| (2) | −20.5 mm |
| (3) | −20.0 mm |
| (4) | −18.5 mm |
| (5) | −8.0 mm |
| (6) | −7.5 mm |
| (7) | +8.0 mm |

Given these results, it is possible to measure differences in capillary fluid height which correlate to differences in affinity for other surfaces and correlate well to printability. As is well known, PTFE would be expected to display extreme hydrophobicity and lack of affinity for inks and other surfaces. Untreated HDPE and LDPE would be expected to be less hydrophobic although sufficiently lacking in affinity for other surfaces to present difficulties in printing and bonding. Corona treated HDPE would be expected to have greater affinity for water and significantly improved printability and bondability. Polyester film is expected to display reasonable affinity for water and good general printability and bondability. Finally, flame treated glass surfaces are expected to have great affinity for water. Certainly, these exact trends are displayed, with a high correlation of fluid height and general expected affinity. In addition, it is obvious that relative comparison of height measured for such surfaces could serve as a simple method for evaluation of bondability, printability, and the like.

Analytical estimation of contact angle between water and these surfaces was also undertaken. Given the width of the reference channel relative to its depth, the effects of the fluid at the sidewalls of the channel were ignored. Given this approximation, the contact angle between the thermoplastic elastomer and the water was calculated using the height obtained with the reference channel sealed over a surface with identical properties. From the theoretical analysis presented above, the contact angle was calculated using the expression $$\theta_{known} = \cos^{-1}(\rho g h d/2\gamma).$$

The density of water, $\rho$, was taken as 1.0 g/cc and the surface tension of water at 22 degrees Celsius, was taken as 69.0 dyne/cm. The acceleration due to gravity was taken to be 9.8 m/s$^2$. This yielded a contact angle estimate of 120 degrees.

Given $\theta_{known}$, the expression $$\theta_{unknown} = \cos^{-1}(\rho g h d/\gamma - \cos(\theta_{known}))$$

was used to estimate the contact angle between water and the other surfaces tested. In each case, $\theta_{known}$ was taken as 121 degrees, and the measured height was substituted into the expression. This yielded the following contact angle estimates:

| Material | Water Contact Angle Estimate |
|---|---|
| (1) | 167° |
| (2) | 123° |
| (3) | 121° |
| (4) | 116° |
| (5) | 84° |

-continued

| Material | Water Contact Angle Estimate |
|---|---|
| (6) | 82° |
| (7) | 22° |

As one of ordinary skill in the art will recognize, various refinements of these estimates are possible, but they serve to clearly illustrate methodology for determining contact angles using embodiments of the invention.

EXAMPLE 2

A second 2-inch long strip was cut from the thermoplastic elastomer casting described in Example 1 to create a second reference channel device. This device was utilized in dynamic contact angle measurements.

The reference channel device was first attached to a thermoplastic elastomer surface cut from the same casting such that all surfaces within the resultant capillary were functionally identical. The resultant capillary was adhered; through its natural adherence, to the inside of the same acrylic vessel utilized for the tests in example 1. The capillary channel was mounted vertically in juxtaposition to the external scale, marked in mm, mounted to the external surface of the vessel. A CCD camera system was focused on the capillary channel, and the camera signal was output to a computer allowing time lapse video imaging of the subsequent experiment.

A precision micro gear pump, with variable speed drive, was then utilized to pump HPLC grade water into the acrylic vessel, at a predetermined and constant rate, as the computer recorded images of the system at a rate of 1 frame per second. As the water was pumped into the vessel at a fixed flow rate, the water bath level rose at a constant rate, ultimately, passing up the vertical exterior of the capillary device. As the water bath level rose, water was eventually forced to rise within the capillary channel at some rate. The bath level was allowed to rise until reaching the top of the capillary device, at which time the experiment was terminated. This procedure was repeated at different rates of fluid flow into the -vessel, providing results at different rates of fluid advancement within the capillary channel.

Subsequently, the time lapse video images of these experiments were examined. At each flow rate, the difference in height between the surface of the water in the bath, and the water rising within the capillary channel, was measured as a function of time. In each case, it was found that, following the onset of fluid flow up the capillary channel, the height of fluid in the channel, relative to the bath surface, quickly achieved a steady state which was maintained, with minor fluctuation, through the remainder of the experiment. Using the video images, the velocity of fluid front rising in the channel was measured, following the achievement of steady state, along with the fluid height in the channel relative to the surface of the water in the bath.

The following table summarizes the results of these experiments:

| Fluid Front Velocity | Height of Fluid in Channel (Rel. to Bath) |
|---|---|
| 0.06 mm/sec | −21.0 mm |
| 0.31 mm/min | −21.0 mm |
| 1.20 mm/sec | −22.0 mm |
| 1.90 mm/min | −21.0 mm |

Clearly, the fluid height in the channel, relative to the water bath level, is little altered by the dynamics of the fluid within the capillary. This result is important for several reasons. First, the lack of a significant change in height, relative to that obtained statically (an average of −21.25 mm vs.−20.0 from example 1), and as a function of increasing velocity, clearly indicates that the contact angle is substantially unaltered by advancement over the surfaces of this particular thermoplastic elastomer formulation. In addition, it is clear that viscous forces, required to cause the water to flow through the capillary, may be ignored (since these forces are, obviously, too small to influence the height measurement significantly under dynamic conditions).

From this data, it is appropriate to estimate that the contact angle between the water and the thermoplastic elastomer walls of the reference channel device, under the conditions given, is approximately 123 degrees. In addition, it is appropriate to consider this contact angle unaltered by dynamic conditions.

Given this result, the reference channel device was attached to another surface known to exhibit changes in contact angle as a function of advancing or receding rate. This surface was that of another thermoplastic elastomer formulation sold commercially by GLS corporation. This material, Dynaflex G6708, was tested in tape form. A swatch of the material was cut and attached to the reference channel device, to form a capillary which was adhered, exactly as above, to the interior of the acrylic vessel.

Again, the micro-pump and video acquisition system were utilized to measure the water height in the capillary, relative to the bath surface, under steady state dynamic conditions as the fluid rose at a constant rate within the capillary. This resulted in the following data:

| Fluid Front Velocity | Height of Fluid in Channel (Rel. to Bath) |
|---|---|
| 0.11 mm/sec | −16.0 mm |
| 0.50 mm/sec | −18.0 mm |
| 1.35 mm/sec | −22.0 mm |

Here, the effect of the rate of advancement over the material surface is apparent.

Given this data, a wide range of analyses are possible. Underlying principles are illustrated through a simple approximate estimate of dynamic contact angle between water and the G6703 surface. Given the general lack of viscous effects, it is possible to ignore the pressures required for the fluid to flow into the capillary purely due to hydrodynamic effects. With this assumption, the forces acting on the fluid column reduce to those already considered in the equilibrium analysis presented in example 1. It is, therefore, appropriate to estimate the dynamic contact angle using the essentially unaltered relationship $$\theta_{known} = \cos^{-1}(\rho g h d/\gamma - \cos \theta_{known}),$$

where $\theta_{known}$ is taken as 123°, and the same water parameters enumerated in example 1 are employed.

This analysis results in the following estimation of the dynamic contact angle against Dynaflex G6708 thermoplastic elastomer surfaces, as a function of advancing fluid rate:

| Fluid Front Velocity | Dynamic Contact Angle Estimate |
|---|---|
| 0.11 mm/sec | 106° |
| 0.50 mm/sec | 112° |
| 1.35 mm/sec | 126° |

Although such an analysis could incorporate a variety of additional effects, including viscous stresses created by fluid flow in the capillary, and perturbations created at the capillary corners and side walls, this analysis provides estimates of dynamic contact angle generally representative of methods enabled by the invention.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A reference channel capillary device comprising: an open capillary channel embedded within a surface of a supportive materials system, the capillary channel having a cross sectional geometry sufficient to create an open channel, the capillary device being configured to form a closed capillary against an adjacent surface, wherein said supportive materials system comprises a thermoplastic elastomer plasticized with mineral oil.

2. A reference channel capillary device as defined in claim 1, wherein the surface in which the open capillary channel is embedded is configured to adhere to an adjacent surface.

3. A reference channel capillary device as defined in claim 2, wherein the surface in which the open capillary channel is embedded includes an adhesive coating.

4. A reference channel capillary device as defined in claim 2, wherein the supportive materials system comprises a polymer having adhesive properties that enables the surface of the supportive materials system to adhere to an adjacent surface.

5. A reference channel capillary device as defined in claim 1, wherein the open capillary channel is embedded within a planar surface.

6. A reference channel capillary device as defined in claim 1, wherein the open capillary channel is embedded within a curved surface.

7. A reference channel capillary device as defined in claim 1, wherein the open capillary channel is embedded within a planar surface and has a rectangular cross section with a depth of less than about 0.020 inches and a width greater than 10 times the depth.

8. A reference channel capillary device as defined in claim 1, wherein the supportive materials system is made from a polymer.

9. A reference channel capillary device as defined in claim 1, wherein the supportive materials system comprises glass.

10. A reference channel capillary device as defined in claim 1, wherein the supportive materials system comprises a ceramic material.

11. A reference channel capillary device as defined in claim 1, wherein the supportive materials system comprises a metal.

12. A reference channel capillary device as defined in claim 1, wherein the supportive materials system comprises a semiconductor.

13. A reference channel capillary device as defined in claim 1, wherein the device is transparent or translucent.

14. A reference channel capillary device as defined in claim 1, wherein a surface of the capillary channel is coated with a layer of material through electrodeposition, evaporation, sputtering, plasma treatment, or chemical vapor deposition.

15. A reference channel capillary device as defined in claim 1, wherein a surface of the capillary channel comprises a polymer which is bonded to the supportive materials system.

16. A reference channel capillary device as defined in claim 1, wherein the supportive materials system is made from a material comprising a styrene ethylene-butylene styrene block copolymer.

17. A reference channel capillary device as defined in claim 16, wherein the styrene ethylene-butylene styrene block copolymer is mixed with a mineral oil and a paraffin wax.

18. A reference channel capillary device comprising:
an open capillary channel embedded within a supportive materials system, the capillary channel having a cross sectional geometry sufficient to create an open channel, the capillary device being configured to form a closed capillary against an adjacent surface, the capillary device further being configured to be placed against a curved adjacent surface for forming the closed capillary, the supportive materials system being made from a material comprising a thermoplastic elastomer plasticized with mineral oil.

19. A reference channel capillary device as defined in claim 18, wherein the device is transparent or translucent.

20. A reference channel capillary device as defined in claim 18, wherein a surface of the capillary channel is coated with a layer of material through electrodeposition, evaporation, sputtering, plasma treatment, or chemical vapor deposition.

21. A reference channel capillary device as defined in claim 18, wherein a surface of the capillary channel comprises a polymer which is bonded to the supportive materials system.

22. A reference channel capillary device comprising:
an open capillary channel defined by a planar surface of a supportive materials system, the capillary device being configured to form a closed capillary against an adjacent planar surface, the capillary channel having a rectangular cross section with a depth of less than about 0.02 inches and a width greater than about 10 times the depth, the supportive materials system being made from a material comprising a polymer, a glass, a semiconductor, a ceramic, a metal, a thermoplastic elastomer plasticized with mineral oil, or mixtures thereof.

23. A reference channel capillary device as defined in claim 22, wherein the device is transparent or translucent.

24. A reference channel capillary device as defined in claim 22, wherein a surface of the capillary channel is coated with a layer of material through electrodeposition, evaporation, sputtering, plasma treatment, or chemical vapor deposition.

25. A reference channel capillary device as defined in claim 22, wherein a surface of the capillary channel comprises a polymer which is bonded to the supportive materials system.

26. A spacer wall capillary device comprising a first spacer element spaced from a second spacer element, the spacer elements being configured to be attached to two opposing adjacent surfaces, the spacer elements holding the surfaces apart thereby producing a capillary, said spacer elements comprise a thermoplastic elastomer plasticized with mineral oil.

27. A spacer wall capillary device, as defined in claim 26, wherein the spacer elements have a thickness of less than about 0.020 inches.

28. A spacer wall capillary device as defined in claim 26, wherein the two spacer elements are initially held some distance apart by a support to facilitate application and creation of a capillary between parallel surfaces.

29. A spacer wall capillary device as defined in claim 26, wherein the spacer elements are made from a material comprising sheets of a polymer, a metal, a ceramic, a glass, or a semiconductor.

* * * * *

UNITED STATES PATENT AND TRADEMARK OFFICE
CERTIFICATE OF CORRECTION

| | |
|---|---|
| PATENT NO. | : 7,024,921 B2 |
| APPLICATION NO. | : 10/703107 |
| DATED | : April 11, 2006 |
| INVENTOR(S) | : Stephen P. Sutton |

It is certified that error appears in the above-identified patent and that said Letters Patent is hereby corrected as shown below:

Col. 20, line 13-16 reads "... comprising a polymer, a glass, a semiconductor, a ceramic, a metal, a thermoplastic elastomer plasticized with mineral oil, or mixtures thereof." should read --...comprising a thermoplastic elastomer plasticized with mineral oil.--

Signed and Sealed this

Tenth Day of July, 2007

JON W. DUDAS
*Director of the United States Patent and Trademark Office*